United States Patent
Fujihira et al.

(10) Patent No.: US 7,166,440 B2
(45) Date of Patent: Jan. 23, 2007

(54) 2,4,5-TRICHLOROPHENOXYALKYL CARBOXYLIC ACID AND A METHOD FOR DETERMINING DIOXINS USING THE SAME

(75) Inventors: Hiroki Fujihira, Hhygo (JP); Kohei Nakatani, Hhygo (JP)

(73) Assignee: Takuma Co., Ltd., Osaka (JP)

( * ) Notice: Subject to any disclaimer, the term of this patent is extended or adjusted under 35 U.S.C. 154(b) by 202 days.

(21) Appl. No.: 10/687,684

(22) Filed: Oct. 17, 2003

(65) Prior Publication Data
US 2004/0191846 A1 Sep. 30, 2004

(30) Foreign Application Priority Data
Mar. 27, 2003 (JP) .............................. 2003-087032

(51) Int. Cl.
*G01N 33/545* (2006.01)
*G01N 33/535* (2006.01)
*C07K 17/02* (2006.01)

(52) U.S. Cl. .................. 435/7.93; 435/7.92; 435/7.95; 530/405; 530/406

(58) Field of Classification Search ................ 562/472; 435/7.92, 7.93, 7.95; 530/405, 406
See application file for complete search history.

(56) References Cited

U.S. PATENT DOCUMENTS

2006/0166296 A1* 7/2006 Nishii et al. ................ 435/7.92

FOREIGN PATENT DOCUMENTS

JP 2002-128731 5/2002
JP 2002-131316 5/2002

OTHER PUBLICATIONS

M. Kawada et al, HCAPLUS 1998: 239541 (abstract of JP A210101615 {19980421}).*
S. Eremin et al, HCAPLUS 1995: 562387 (abstract of Voprosy Meditsinskoi Khimii (1994), 40(4), 57-60.*
D. Rinder et al, HCAPLUS 1981: 401702 (abstract of Bull. Environmental Contamiination and Toxicology (1981), 26(3), 375-480.*
English language translation of Japanese Laid Open Patent Publication 10101615, published Apr. 21, 1998.*
Yukio Sugawara, Shirley J. Gee, James R. Sanborn, S. Douglass Gilman, Bruce D. Hammock, Development of a Highly Sensitive Enzyme Linked Immunosorbent Assay Based on Polyclonal Antibodies for the Detection of Polychlorinated Dibenzo-p-dioxins, 1998, pp. 1092-1099, vol. 70, California, Analytical Chemistry, No. 6.
Kun Chae, Lee Kyung Cho, James D. McKinney, Synthesis of 1-Amino-3,7,8-trichlorodibenzo-p-dioxin and 1-Amino-2,3,7,8,-tetrachlorodibenzo-p-dioxin as Haptenic Compounds, 1977, pp. 1207-1209, vol. 25, No. 5, J. Agricultural and Food Chemistry.
Simona G. Merica, Nigel J. Bunce, Synthesis of nitropolychlorinated dibenzo-p-dioxins (NPCDDs) and their photochemical reaction with nucleophiles, 1995, pp. 826-834, vol. 73, Canada, Can.-J. Chem.
Hiroki Fujihira, Kohei Nakatani, Shigeaki Nishii, Kazuhiro Matsui, Development of the conventional analysis method for the dioxins using ELISA, The 5th Annual Meeting of Japan Society of Endocrine Disrupters Research, 2002, p. 86. Japan, Abstract only.
Ya-Wen Chiu, Robert E. Carlson, Karen L. Marcus, Alexander E. Karu, A Monoclonal Immunoassay for the Coplanar Polychlorinated Biphenyls, 1995, pp. 3829-3831, vol. 67. California, No. 1, Analytical Chemistry.
Press Release via internet by Takuma and Toyobo, Development of high sensitive and rapid determination of dioxins, Dec. 3, 2002, Japan, Translation of lines 6 to 7 from title.

\* cited by examiner

*Primary Examiner*—Mary E. Ceperley
(74) *Attorney, Agent, or Firm*—Amin, Turocy&Calvin, LLP

(57) ABSTRACT

An immunoassay of dioxins using 2,4,5-trichlorophenoxy-alkyl amide derivative represented by the following formula (II) as an antigen for a competitive immunoassay is provided:

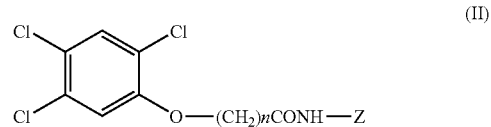

(II)

where n is an integer of 1 to 10, and Z is a carrier compound or a label. This compound is not toxic, and is specific to dioxins and can be conjugated with a wide range of dioxin isomers, so that a safe and simple assay of dioxins can be provided.

4 Claims, 2 Drawing Sheets

2,4,5-TRICHLOROPHENOXYALKYL CARBOXYLIC ACID AND A METHOD FOR DETERMINING DIOXINS USING THE SAME

BACKGROUND OF THE INVENTION

1. Field of the Invention

The present invention relates to 2,4,5-trichlorophenoxyalkyl amide derivatives and an immunoassay of dioxins using the same.

2. Description of the Related Art

The term "dioxins" is a general term for polychlorinated dibenzo-p-dioxins (PCDDs), polychlorinated dibenzofurans (PCDFs) and coplanar polychlorinated biphenyl (Co-PCBs). For PCDDs and PCDFs, there are a very large number of isomers, such as 75 and 135 isomers, respectively, depending on the number and the position of chlorines, and the intensity of toxicity is considerably different from isomer to isomer. In particular, in PCDD and PCDF isomers, isomers having chlorine at the 2-, 3-, 7- and 8-positions are highly toxic. Examples of the toxic symptoms include thymus atrophy, liver hypertrophy, exhaustion and starvation symptoms, and chloric acne. Furthermore, it is known that long exposure to dioxin, even though only in a low amount, causes chronic symptoms such as porphyria cutanea tarda, and exhibits a variety of toxicity such as teratogenicity, carcinogenicity and cocarcinogenicity.

Furthermore, in recent years, it has become known that a certain type of compounds has the effect of disturbing the endocrine function of organisms, and these compounds, which are so-called "endocrine disturbing chemicals", have gained attention as a global environmental problem. It also has been found that the dioxins are possible endocrine disturbing chemicals having estrogen activity.

It has become evident that dioxins having such various toxicities are contained in chemical products such as herbicides or insecticides, exhaust gas and fly ash released from incineration plants, or drains from paper mills. For this reason, dioxins are detected not only in samples derived from environments such as water, bottom sediments of rivers or harbors around big cities, air, soil or the like, but also in samples derived from organisms such as food, blood, mother milk, or urine, and pollution is wide-spread, which is regarded as a problem. Thus, since the dioxins in the environment cause a large social problem, it is a pressing task to determine the amount of the dioxins present in the environment.

For determining the dioxins, analytical values with a high precision are required, so that in general, the determination of the dioxins is performed according to an official method of analysis. In this analysis method, various types of chromatography used for extraction, concentration, purification or the like, and equipment including an expensive analysis device such as a high resolution gas chromatograph mass spectrometer are used. The official method of analysis is highly sensitive and can perform multicomponent analysis in which a plurality of compounds can be identified and determined quantitatively at a time. However, this method requires expensive and special equipment and a facility such as a clean room, and also requires a skilled technique for the analysis. Furthermore, it takes time to obtain results because of the complexity of the pre-treatment. Therefore, there is a demand for development of a highly precise and simple determining method. In order to solve this problem, there is a demand for a method for determining dioxins by an immunoassay utilizing a comparatively inexpensive and simple antigen-antibody reaction.

The immunoassay is a method for detecting a trace amount of an antigen using the ability of an antibody to recognize an antigen specifically, and the antigen can be determined with high sensitivity by utilizing the high affinity and the high specificity of the antibody to the antigen. The pre-treatment of samples is simple, so that multiple samples can be determined simply and rapidly, and the cost for the determination is low. Thus, this method is advantageous, so that it is widely used for medicine, biochemistry, pharmacology, agriculture and the like.

It is necessary to recognize an antibody or an antigen in order to detect a substance to be determined in the immunoassay, and various labels are used. Examples of the immunoassay include enzyme immunoassay (EIA), radioimmunoassay (RIA), and fluorescence immunoassay (FIA), which are defined depending on the type of the label. In all of these immunoassays, a calibration curve is obtained by performing an assay with the same compound as a compound to be determined in the same manner as for a sample, and the compound concentration in the sample is calculated based on this calibration curve.

In general, in the determination in clinical tests or the biochemical field, the EIA is utilized because of its simplicity, and the EIA is also attempted to be used for the determination of the dioxins. However, for the dioxins, there are three types having a specific basic structure, as described above. There are a large number of isomers having a different number of chlorine substituents. Therefore, there is a problem as to which compound should be used as the indicator. For example, many of the developed EIA determination systems of dioxins is aimed to determine 2,3,7,8-tetrachlorozibenzo-p-dioxin (2,3,7,8-TeCDD), which is the most toxic substance among the dioxins. Using this toxic substance as a standard, determination of the dioxin has been performed (see Anal. Chem., vol.70, pp. 1092–1099).

However, in the above described assays, since the antigens, such as labeled antigens or solid-phase antigens, are prepared by highly toxic substances, carefully handling and disposal of these toxic antigens is required, which restricts the use of the assay.

Therefore, if a compound other than a toxic compound can be used as an antigen, handling can be easy and a safe and rapid assay for dioxins can be provided. Japanese Laid-Open Patent Publications Nos. 2002-128731 and 2002-131316 propose compounds alternative to PCB, but no compound specific to dioxins has been provided yet.

SUMMARY OF THE INVENTION

It is an object of the present invention to solve the above problems, and to provide a compound that can serve as an antigen for immunoassay for determining dioxins in an environmental sample in a simple manner, and to provide an immunoassay for dioxins using this compound as an antigen.

The inventors of the present invention found as a result of in-depth research that 2,4,5-trichlorophenoxyalkyl carboxylic acid is useful as an antigen for competitive immunoassay in the EIA determination systems of dioxins and achieved the present invention.

The present invention provides a 2,4,5-trichlorophenoxy-alkyl carboxylic acid represented by the following formula (I):

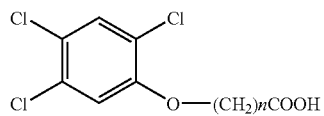

where n is an integer of 1 to 10.

Furthermore, the present invention provides an immunoassay of dioxins, wherein the 2,4,5-trichlorophenoxyalkyl carboxylic acid is used as an antigen for a competitive immunoassay.

According to another aspect of the present invention, the present invention provides a 2,4,5-trichlorophenoxyalkyl amide derivative represented by the following formula (II):

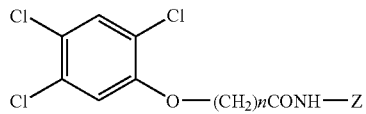

where n is an integer of 1 to 10, and Z is a carrier compound or a label.

Furthermore, the present invention provides an immunoassay of dioxins, wherein the 2,4,5-trichlorophenoxyalkyl amide derivative is used as an antigen for a competitive immunoassay.

According to another aspect of the present invention, the present invention provides an immunoassay kit for dioxins comprising a 2,4,5-trichlorophenoxyalkyl carboxylic acid represented by the following formula (I):

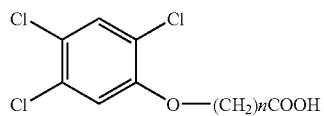

where n is an integer of 1 to 10, or a 2,4,5-trichlorophenoxyalkyl amide derivative represented by the following formula (II):

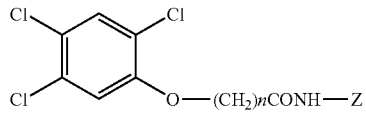

where n is an integer of 1 to 10, and Z is a carrier compound or a label.

In a preferable embodiment, the kit comprises 2,4,5-trichlorophenoxyalkyl amide derivative (II) which is immobilized to a solid phase as an antigen, a primary antibody to dioxins and a labeled secondary antibody to the primary antibody.

DESCRIPTION OF THE PREFERRED EMBODIMENT

The Compound of the Present Invention

Figure 1:
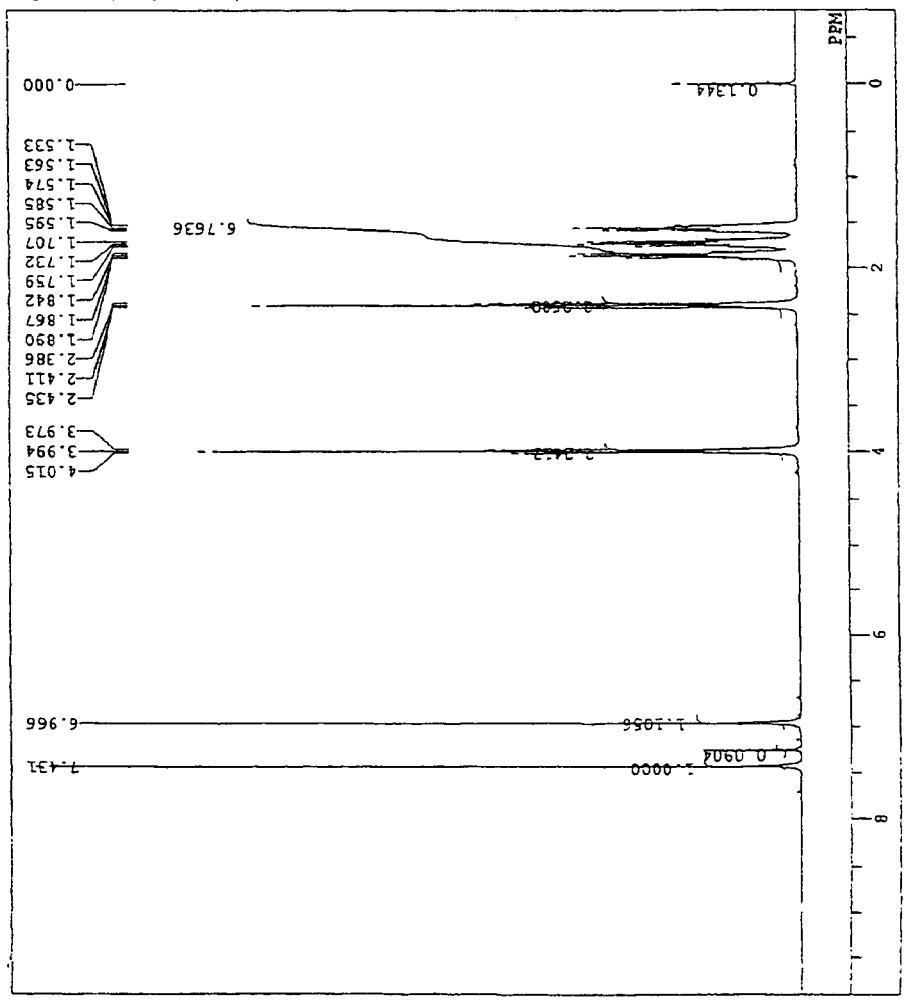
FIG. 1 is a graph showing the physical property data (NMR) of 6-(2,4,5-trichlorophenoxy) hexanoic acid (Ia).

The 2,4,5-trichlorophenoxyalkyl carboxylic acid of the present invention can be represented by the following formula (1):

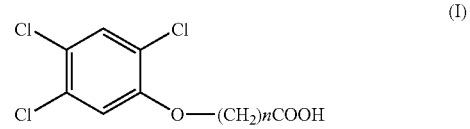

where n is an integer from 1 to 10. Hereinafter, this substance may be referred to as "compound (I)". In this compound (I), n is preferably 3 to 8, and more preferably 5 to 7. This compound (I) can be succinimidylated, and conjugated to a carrier protein (e.g., bovine serum albumin (BSA)) as described later, and thus can be used as an antigen for a competitive immunoassay.

The 2,4,5-trichlorophenoxyalkyl amide derivative can be represented by the following formula (II):

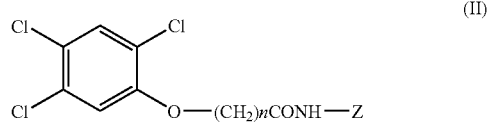

where n is an integer from 1 to 10, and Z is a carrier compound or a substance for labeling. Hereinafter, this substance may be referred to as "compound (II)". In this compound (II), n is preferably 3 to 8, and more preferably 5 to 7. This compound (II) can be derived from the compound (I). As a carrier compound of Z, for example, an amino acid or a protein can be used. The compound (II) is immobilized in the solid phase via the residue of the amino acid or the protein. As a label, for example, horseradish peroxidase (HRP), alkaline phosphatase (ALP) or the like can be used.

Synthesis of the Compounds (I) and (II)

The compounds (I) and (II) can be synthesized in the following manner, for example.

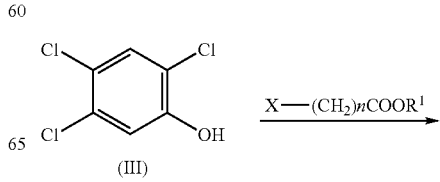

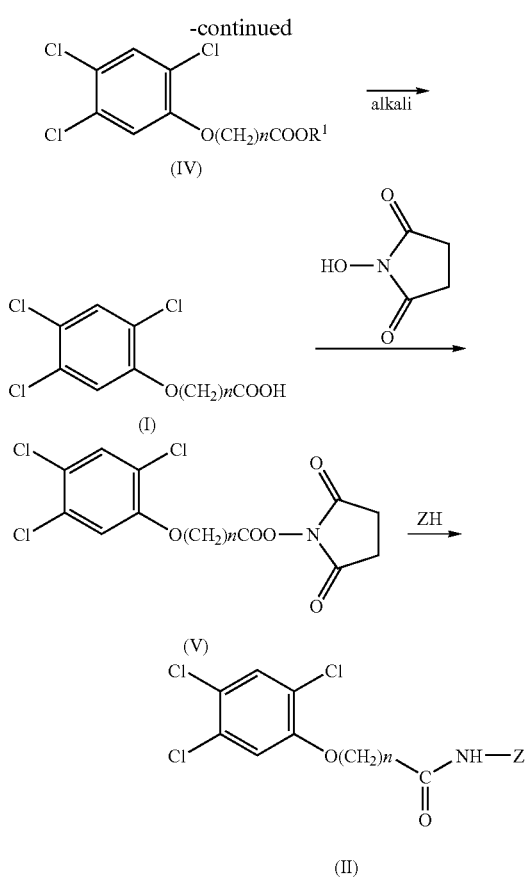

First, 2,4,5-trichlorophenol (III) is reacted with a halogenated fatty acid alkyl ester to form 2,4,5-trichlorophenoxyalkyl carboxylic acid alkyl ester (IV). Then, this ester (IV) is saponified with alkali, so that the compound (I) can be obtained. The obtained compound (I) is reacted with N-hydroxy succinimide to synthesize the activated ester shown in formula (V), and then reacted with a compound containing an amino group such as an amino acid (glycine, etc.) and peptide, and thus the compound (II) is obtained.

In the above scheme, the halogenated fatty acid alkyl ester is represented by $X-(CH_2)_nCOOR^1$, where X is a halogen, $R^1$ is an alkyl group, and n is an integer of 1 to 10. The compound containing an amino group such as an amino acid and peptide is represented by ZH.

Immunoassay

In the immunoassay of dioxins of the present invention, a 2,4,5-trichlorophenoxyalkyl amide derivative (II) is used as a competitive antigen. The manner of the assay is the same as that of the conventional immunoassays. The immunoassays include enzyme immunoassay (EIA), radioimmunoassay (RIA), and fluorescence immunoassay (FIA), and there is no particular limitation regarding the immunoassay in the present invention. In these immunoassays, the determination can be performed in the manner such as a competitive assay, a non-competitive assay, or a homogeneous assay. Since the dioxins are low molecular weight compounds, the determination is generally performed by a competitive assay. For the competitive assay, there are generally an indirect competitive assay in which an antigen is immobilized on a well of a microplate or a tube, and a direct competitive assay in which an antibody is immobilized on a well or a tube.

Among the above-described immunoassays, it is preferable to employ EIA because of its simplicity of the determination. Hereinafter, the present invention will be described by taking as an example the cases that the dioxins are determined by an indirect competitive assay or by a direct competitive assay, both utilizing EIA.

An example of determination by an indirect competitive assay will be described below. First, 2,4,5-trichlorophenoxyalkyl amide derivative (II) (compound (II)) is used as an antigen and immobilized on a solid phase such as a well of a microplate via the Z portion. Then, the surface of the solid phase that is not conjugated to the compound (II) is blocked with a commercially available blocking agent such as bovine serum albumin or casein.

Then, an anti-dioxin antibody is prepared. This antibody can be produced in the following manner. A dioxin is haptenized according to a method used by a skilled person in the art, and the haptenized dioxin is conjugated to a carrier protein such as bovine serum albumin so as to prepare a conjugate. Then, a mammal is immunized to the conjugate as an immune antigen (see Kun Chae, et al., J. Agric. Food., 25, 1207–1209 (1977); Simona G. Merica, et al., Can. J. Chem., 73, 826–834 (1995)). This anti-dioxin antibody can be used as a primary antibody in the present invention. The anti-dioxin antibody can be either a polyclonal antibody or a monoclonal antibody. In view of homogeneity, the monoclonal antibody is preferable.

Then, the anti-dioxin antibody and a sample are brought into contact with the compound (II) that is immobilized on the solid phase. That is, dioxins in the sample and the compound (II), a solid-phase antigen, are subjected to a competitive reaction with the anti-dioxin antibody (a primary antibody). Then, the reaction mixture is removed, followed by washing the solid phase to remove the anti-dioxin antibody (primary antibody) that was not bound to the compound (II). Then a labeled anti-immunoglobulin antibody (labeled secondary antibody) is added so as to react with the primary antibody that is bound to the solid phase. Then, the reaction mixture was removed, followed by washing the solid phase to remove the labeled secondary antibody that was not bound to the primary antibody. Then, the label of the secondary antibody that is bound to the primary antibody is detected. From the measured values, the dioxin concentration in the sample is calculated, based on the calibration curve previously prepared using the primary antibody and the labeled secondary antibody while varying the concentration of the compound (II).

On the other hand, the determination by the direct competitive assay is performed as follows. First, an anti-dioxin antibody is immobilized on a solid phase such as a well, and blocking is performed. A labeled compound (II) and a sample are provided thereto so that the solid-phase antibody, the sample, and the labeled compound (II) are subjected to a competitive reaction. After the solid phase is washed, label is detected in the same manner as in the indirect competitive assay. From the measured values, the dioxin concentration in the sample is calculated, based on the calibration curve previously prepared using a competition with respect to the solid-phase anti-dioxin antibody while varying the ratio of the labeled compound (II) and the non-labeled compound (II).

In the indirect competitive assay, a primary antibody is labeled, and in the direct competitive assay, an antigen (compound (II)) is labeled. As the label, for example, enzymes such as HRP or ALP, a fluorescent substance such as rhodamine, or a chemiluminescent substance can be used. The labeling of the compound (II) can be performed by a method that is commonly used by those skilled in the art, for example, by bringing the compound (II) in contact with the label in a buffer solution. In each method of EIA, RIA and FIA, detection is performed by a method employed by ordinary skilled in the art depending on the kind of the label.

The 2,4,5-trichlorophenoxyalkyl amide derivative (II) of the present invention has no toxicity coefficient, and has the property of reacting with an anti-dioxin antibody. Therefore, in a competitive immunoassay of the present invention, it is not necessary to use a highly toxic dioxin for determining dioxins as the competitive antigen. Thus, the safety of an operator during operation can be guaranteed.

(Immunoassay Kit)

The kit of a present invention comprises compound (I) or compound (II) as an antigen. Preferably, the compound (II) is immobilized to a solid phase, such as plate. Therefore, the kit of the present invention comprises a plate on which compound (II) is immobilized, an antibody to dioxins (a primary antibody), and an antibody to the primary antibody (a secondary antibody). These components are included in a separate manner. As antigens, the primary antibody and the secondary antibody employed in the kit of the present invention are as described. The kit of the present invention can include an apparatus to detect the label, for example, calorimeter.

EXAMPLES

Hereinafter, the present invention will be described more specifically by way of examples, but the present invention is not limited thereto.

Example 1

Preparation of 6-(2,4,5-trichlorophenoxy) hexanoic acid (Ia)

First, 987 mg (5 mmol) of 2,4,5-trichlorophenol (III) and 1.04 g (7.5 mmol) of anhydrous potassium carbonate were added to 8 ml of anhydrous dimethyl formamide and the mixture was stirred. Then, 1.67 g (7.5 mmol) of 6-bromohexanoic acid ethyl ester was added thereto, and the mixture was stirred at 60° C. for 16 hours. After the reaction was completed, the solvent was concentrated under reduced pressure. The residue was extracted with dichloromethane, washed with water, and was then concentrated under reduced pressure to dryness. The residue was dissolved in a mixed solution of 10 ml of dioxane and 12.5 ml of methanol, and 2.5 ml of 10 N sodium hydroxide was added thereto with stirring. The mixture was stirred at room temperature for 6 hours. After the reaction was completed, 5 ml of water was added to the mixture and neutralized with 6 N hydrochloric acid. The solvent was evaporated under reduced pressure to dryness, 1 N hydrochloric acid was added to the residue and the residue was extracted with chloroform. After washing with water, the residue was concentrated under reduced pressure to dryness and was powdered using a mixed solution of hexane and ether to obtain 6-(2,4,5-trichlorophenoxy) hexanoic acid (Ia) (hereinafter, referred to as "compound (Ia)") in an amount of 1.32 g (yield: 85%).

FIG. 1 shows the physical property data (NMR) of the 6-(2,4,5-trichlorophenoxy) hexanoic acid (Ia) thus obtained.

Example 2

Preparation of 6-(2,4,5-trichlorophenoxy) hexanoic acid amide Derivative (IIa)

Using the compound (Ia) obtained in Example 1, 6-(2,4, 5-trichlorophenoxy) hexanoic acid amide derivative (compound (IIa)) that can be used as an antigen for a competitive assay was prepared by an active ester method in the following manner. First, 312 mg (1 mmol) of the compound (Ia), 138 mg (1.2 mmol) of N-hydroxysuccinimide and 152 mg (1.5 mmol) of triethyl amine were dissolved in 4 ml of anhydrous dimethyl formamide. After 288 mg (1.5 mmol) of 1-ethyl-3-(3'-diethylaminopropyl) carbodiimide hydrochloride was added thereto, the mixture was stirred at room temperature for 16 hours. After the reaction was completed, the solvent was evaporated under reduced pressure, and the residue was extracted with chloroform. After washing with water, the organic layer was concentrated under reduced pressure to dryness. The residue was purified with silica gel column chromatography (eluted with dichloroethane:ethyl acetate=4:1) to obtain succinimidyl 6-(2,4,5-trichlorophenoxy) hexanoate (Va) (hereinafter, referred to as "compound (Va)") in an amount of 360 mg (yield: 88%).

Figure 2:
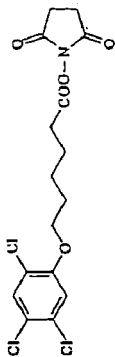
FIG. 2 is a graph showing the physical property data (NMR) of succinimidyl 6-(2,4,5-trichlorophenoxy) hexanoate (Va).

FIG. 2 shows the physical property data (NMR) of succinimidyl 6-(2,4,5-trichlorophenoxy) hexanoate (Va).

6-(2,4,5-Trichlorophenoxy) hexanoic acid amide derivative (IIa) was prepared by conjugating the obtained compound (Va) with bovine serum albumin (BSA), which is a carrier protein, in the manner shown below.

First, to 1 ml of 50 mM phosphate buffer (pH 8.0) which contains equivalent to 15 mg of BSA ($2.27 \times 10^{-7}$ mol), 545.5 µl of dimethylsulfoxide (DMSO) was added with stirring under ice cooling. Thereafter, 454.5 µl of a DMSO solution in which compound (Va) was dissolved so as to be 20 mM (40 equivalents: $9.09 \times 10^{-6}$ mol) was dropped thereto and allowed to react at room temperature for one hour. The reaction mixture was loaded to a gel filtration column PD-10 (manufactured by Amersham Bioscience) that was previously equilibrated with a 10 mM phosphate buffered saline (pH 7.2) (PBS), eluted with the PBS, and 1.5 ml of a fraction eluted from 3.5 ml to 5.0 ml was collected. This fraction contains a reaction product (compound (IIa)) of the compound (Va) and BSA. Then, this fraction was diluted with PBS to 2.0 ml so as to obtain a compound (IIa) at a concentration of about 5 mg/ml. The obtained compound (IIa) can be used as an antigen for competitive immunoassays.

Example 3

Evaluation of the Compound of the Present Invention

Using various monoclonal antibodies, the specificity of the monoclonal antibodies to dioxin isomers was examined. The monoclonal antibodies were prepared in the following manner. An antibody-producing cell was injected into the abdominal cavity of a pristane-pretreated mouse. Th ascites fluid in the abdominal cavity caused by the growth of the cells was collected, and then a monoclonal antibody was purified by affinity chromatography using a protein G-Sepharose (manufactured by BIO-RAD Co.) as a carrier.

Using three antibody-producing clones C-1, C-2 and C-3, respective monoclonal antibodies were prepared. The clones C-1, C-2 and C-3 produce monoclonal antibodies with respect to dibenzodioxin having chlorine atom at the 2-, 3-, 7-, and 8-positions.

To evaluate the specificity of the monoclonal antibody was performed according to the following principles. A solid-phase antigen (competitor) and a free dioxin (ligand) are allowed to compete with each other with respect to a free monoclonal antibody (anti-dioxin antibody). If the reactivity of the monoclonal antibody and the dioxin is higher than that of the monoclonal antibody and the solid-phase antigen, the binding of the monoclonal antibody to the solid-phase antigen is reduced. This reduction of the binding of the monoclonal antibody to the solid-phase antigen can be measured by color development method. This phenomenon can be applied to evaluate the specificity.

First, the immune antigen or the compound (IIa) conjugated with BSA that was produced in Example 2 was diluted with PBS to 1 µg/ml, and divided into each well of a 96-well assay plate (manufactured by Costar, Cat. No. 3590) in an amount of 50 µl. Then, the plate was sealed and allowed to stand at room temperature for one hour. Then, each well was washed with PBS containing 0.005% of Tween 20 three times. Next, 300 µl of Block Ace (manufactured by Snow Brand Milk Products Co., Ltd.) diluted with distilled water to a concentration of 25% was supplied to each well, and the plate was sealed and allowed to stand at 37° C. for two hours. Each well was washed with PBS containing 0.005% of Tween 20 three times. Then, a 25 µl of the dioxin compound solution of a final concentration of $5 \times 10^{-7}$ M was added to each well. The dioxin compound solution was prepared by diluting the dioxin with a dilution solvent comprising 20% DMSO and 0.01% of Triton X100. As controls, a dilution solvent in an amount of 25 µl was added to each well. Immediately after the addition of the dioxin compound solution or the dilution solvent, 25 µl of an antibody solution diluted with PBS containing 1 mg/ml of BSA was added to each well. The assay plate was stand at room temperature for one hour with slightly shaking.

After washing with PBS containing 0.005% of Tween 20 three times, 50 µl of the diluted HRP-labeled goat anti-mouse IgG (H+L) antibody (produced by affinity purification) was added to each well. The diluted HRP-labeled antibody was prepared by diluting the purchased HRP-labeled antibody to 2000 times as much with 10% Block Ace. The plate was allowed to stand at room temperature for one hour, followed by washing with PBS containing 0.005% of Tween 20 three times. Then, 50 µl of a HRP substrate, TMB (manufactured by KPL Co., Ltd.), was added to each well and allowed to stand at room temperature for 5 to 10 min. Then, 5 µl of a 1 M phosphate solution was added to each well, and the absorbance at a wavelength of 455 nm (655 nm for the reference) was measured with a spectrophotometer for a microtiter. The reactivity was evaluated by obtaining the absorbance ($B_0$) at the time when the dioxin compound is not added, which is a control (diluent) and the absorbance (B) at the time when the dioxin compound is added. The inhibition rate was measured based on the following equation.

Inhibition rate=$\{(B_0-B)/B_0\} \times 100$ (%)

Evaluation was such that the larger this inhibition rate is, the higher the specificity of the anti-dioxin antibody to the dioxin compound. The results are shown in Table 1.

TABLE 1

| | clone No. | | | | | |
|---|---|---|---|---|---|---|
| solid-phase antigen | C-1 immunogen 1 | C-1 * | C-2 immunogen 2 | C-2 * | C-3 immunogen 3 | C-3 * |
| 2,3,7,8-TeCDD | 0.4 | 7.4 | −3.0 | 7.7 | −0.2 | −3.4 |
| 1,2,3,7,8-PeCDD | 21.3 | 46.2 | 45.7 | 70.4 | 5.4 | 31.2 |
| 1,2,3,4,7,8-HxCDD | −1.4 | 14.1 | −9.4 | 19.1 | −2.5 | −2.3 |
| 1,2,3,6,7,8-HxCDD | 3.1 | −0.3 | −6.2 | 2.2 | 3.9 | 6.7 |
| 1,2,3,7,8,9-HxCDD | 15.7 | 19.1 | 30.6 | 41.9 | 6.7 | 28.6 |
| 1,2,3,4,6,7,8-H$_p$CDD | 1.5 | 1.4 | −12.4 | −3.2 | 0.4 | 2.1 |
| OCDD | −2.5 | 1.6 | 0.1 | 9.4 | −0.4 | −3.7 |
| 2,3,7,8-TeCDF | 1.6 | 8.4 | 15.3 | 37.6 | −1.6 | 4.3 |
| 1,2,3,7,8-PeCDF | 11.8 | 27.1 | 17.5 | 68.6 | 0.5 | 23.2 |
| 2,3,4,7,8-PeCDF | 26.5 | 40.1 | 40.2 | 55.0 | 13.0 | 46.2 |
| 1,2,3,4,7,8-HxCDF | 3.3 | −1.5 | 5.2 | −11.2 | 4.9 | 0.8 |
| 1,2,3,6,7,8-HxCDF | 3.5 | 7.0 | 9.4 | 5.0 | 2.9 | 4.1 |
| 1,2,3,7,8,9-HxCDF | 26.2 | 34.7 | 43.3 | 68.1 | 10.4 | 48.1 |
| 2,3,4,6,7,8-HxCDF | 31.1 | 44.8 | 28.1 | 82.8 | 13.2 | 47.9 |
| 1,2,3,4,6,7,8-H$_p$CDF | −0.9 | 7.5 | 6.8 | 51.4 | −2.7 | 3.4 |
| 1,2,3,4,7,8,9-H$_p$CDF | 5.8 | 7.1 | 27.7 | 7.5 | 6.1 | 11.3 |
| OCDF | 1.1 | 27.0 | 18.1 | 7.2 | 1.3 | 4.9 |

* a haptenized product of 6-(2,4,5-trichlorophenoxy) hexanoic acid amide derivative The immunogens 1 to 3 in Table 1 show haptenized products of dibenzodioxins, which are immune antigens and have halogen atoms at the 2-, 3-, 7- and 8-positions, and * shows a haptenized product of 6-(2,4,5-trichlorophenoxy) hexanoic acid amide derivative (IIa).

The results of Table 1 indicate that the compound of the present invention including 2,4,5-trichlorophenoxyalkyl carboxylic acid (compound (I)a) and 2,4,5-trichlorophenoxyalkyl amide derivative (compound (IIa) can be used as solid-phase antigens. Further, a far more sensitive determination system can be provided than in the case where the immune antigens such as heptenized dioxins are used as the solid-phase antigen.

Example 4

Evaluation of Specificity to a Chlorine-containing Organic Compound

An anti-dioxin antibody (monoclonal antibody) to 1,2,3,7,8-PeCDF is used as an antibody. A haptenized product of a solid-phase antigen 6-(2,4,5-trichlorophenoxy) hexanoic acid amide derivative (IIa) and the chlorine-containing organic compounds in Tables 2 and 3 were allowed to compete with each other to this anti-dioxin antibody so that a competitive reaction was effected in the same manner as in Example 3. Then, the cross-reactivity was examined. The dioxins used in the experiment have the toxicity equivalent factor (TEF value) shown in Table 2. The results are shown in Tables 2 and 3.

TABLE 2

| dioxins having TEF | TEF value | cross reaction (%) |
|---|---|---|
| 2,3,7,8-TeCDD | 1 | 1.1 |
| 1,2,3,7,8-PeCDD | 1 | 29.9 |
| 1,2,3,4,7,8-HxCDD | 0.1 | 24.8 |
| 1,2,3,6,7,8-HxCDD | 0.1 | 18.0 |
| 1,2,3,7,8,9-HxCDD | 0.1 | 39.8 |
| 1,2,3,4,6,7,8-HpCDD | 0.01 | 17.0 |
| 1,2,3,4,6,7,8,9-OCDD | 0.0001 | <0.1 |
| 2,3,7,8-TeCDF | 0.1 | 1.5 |
| 1,2,3,7,8-PeCDF | 0.05 | 100.0 |
| 2,3,4,7,8-PeCDF | 0.5 | 16.1 |
| 1,2,3,4,7,8-HxCDF | 0.1 | 45.9 |
| 1,2,3,6,7,8-HxCDF | 0.1 | 36.6 |
| 1,2,3,7,8,9-HxCDF | 0.1 | 42.7 |
| 2,3,4,6,7,8-HxCDF | 0.1 | 43.8 |
| 1,2,3,4,6,7,8-HpCDF | 0.01 | 17.9 |
| 1,2,3,4,7,8,9-HpCDF | 0.01 | 28.7 |
| 1,2,3,4,6,7,8,9-OCDF | 0.0001 | 8.0 |

TABLE 3

| | cross reaction (%) |
|---|---|
| polycyclic aromatic hydrocarbons | |
| Anthracene | <0.1 |
| Naphthalene | <0.1 |
| Fluoranthene | <0.1 |
| Pyrene | <0.1 |
| Fluorene | <0.1 |
| Benz[a]anthracene | <0.1 |
| Benzo[b]fluoranthene | <0.1 |
| Benzo[k]fluoranthene | <0.1 |
| Benzo[ghi]perylene | <0.1 |
| Chrysene | <0.1 |
| Indeno[1,2,3-cd]pyrene | <0.1 |
| Phenanthrene | <0.1 |
| 1,2,3,7,8-PeCDF | 100.0 |
| coplanar PCBs | |
| 3,3',4,4'-TeCB | <0.1 |
| 3,3',4,4',5-PeCB | <0.1 |
| 3,3',4,4',5,5'-HxCB | <0.1 |
| chlorobenzens, chlorophenols | |
| m-Dichlorobenzene | <0.1 |
| 1,2,3-Trichlorobenzene | <0.1 |
| 2,4-Dichlorophenol | <0.1 |
| 3,4-Dichlorophenol | <0.1 |
| 2,4,5-Trichlorophenol | <0.1 |
| others | |
| p-chlorobiphenyl | <0.1 |

These results indicate that the compound of the present invention can react specifically with dioxins and a wide range of dioxin isomers. As shown in the Table 3, cross reaction with polycyclic arokmatic hydrocarbons and the chlorinated compounds such as PCBs, chlorobenzenes, chlorophenols are not occurred. Therefore, the compound of the present invention can attain the effect that dioxins can be specifically detected.

The present invention provides a novel 2,4,5-trichlorophenoxyalkyl carboxylic acid (compound (I)) and 2,4,5-trichlorophenoxyalkyl amide derivative (compound (II)). The compound (I) and the compound (II) are used as antigens by an immunoassay. In particular, the compound (II) is used as a solid-phase antigen for an indirect immunoassay, and a wide range of dioxin isomers can be detected and determined specifically. The immunoassay of the present invention can be applied widely to the analysis of dioxins in environmental samples such as air, exhaust gas, soil, river, and combustion ash, and also is useful in the analysis of biological samples such as food, mother milk, blood and urine. This assay eliminates the necessity of using a highly toxic dioxin, so that the safety during the operation of an assay can be improved significantly.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. An immunoassay for determining an amount of dioxins in a sample comprising:

subjecting the sample and a competitive antigen for dioxins to a competitive reaction with an anti-dioxin antibody for a time and under conditions where two immunocomplexes are formed, wherein one immunocomplex is formed between dioxins in the sample and the anti-dioxin antibody and another immunocomplex is formed between the competitive antigen for dioxins and the anti-dioxin antibody, wherein the competitive antigen for dioxins is a 2,4,5-trichlorophenoxyalkyl carboxylic acid represented by the following formula (I):

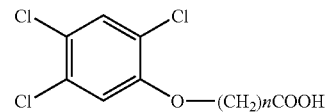

(I)

where n is an integer of 1 to 10;

determining formation of the immunocomplex between the competitive antigen for dioxins and the anti-dioxin antibody by a competitive immunoassay procedure; and calculating the amount of dioxins based on the formation of the immunocomplex between the competitive antigen for dioxins and the anti-dioxin antibody.

2. An immunoassay for determining an amount of dioxins in a sample comprising:

subjecting the sample and a 2,4,5-trichlorophenoxyalkyl amide derivative to a competitive reaction with an anti-dioxin antibody for a time and under conditions where two immunocomplexes are formed, wherein one immunocomplex is formed between dioxins in the sample and the anti-dioxin antibody and another immunocomplex is formed between the 2,4,5-trichlorophenoxyalkyl amide derivative and the anti-dioxin antibody, wherein the 2,4,5-trichlorophenoxyalkyl amide derivative is represented by the following formula (II):

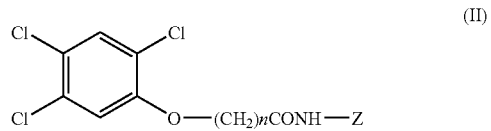

(II)

where n is an integer of 1 to 10, and Z is an amino acid or peptide;

determining formation of the immunocomplex between the 2,4,5-trichlorophenoxyalkyl amide derivative and the anti-dioxin antibody by a competitive immunoassay procedure; and calculating the amount of dioxins based on the formation of the immunocomplex between the 2,4,5-trichlorophenoxyalkyl amide derivative and the anti-dioxin antibody.

3. An immunoassay kit for determining an amount of dioxins in a sample comprising:

a 2,4,5-trichlorophenoxyalkyl carboxylic acid represented by the following formula (I):

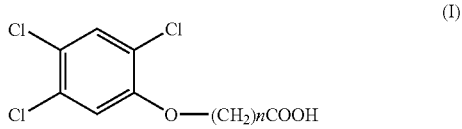
(I)

where n is an integer of 5 to 10, or a 2,4,5-trichlorophenoxyalkyl amide derivative represented by the following formula (II):

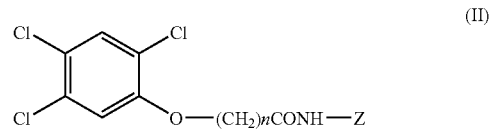
(II)

where n is an integer of 1 to 10, and Z is an amino acid or a peptide;

a primary antibody to dioxins; and a labeled secondary antibody to the primary antibody;

wherein the 2,4,5-trichlorophenoxyalkyl carboxylic acid or 2,4,5-trichlorophenoxyalkyl amide derivative is used as a competitive antigen that reacts specifically with the anti-dioxin antibody and does not cross react with chlorobenzenes and chlorophenols.

4. The immunoassay kit according to claim 3, wherein the kit comprises 2,4,5-trichlorophenoxyalkyl amide derivative (II) which is immobilized to a solid phase.

* * * * *